United States Patent
Jia (10) Patent No.: US 6,759,397 B2
(45) Date of Patent: Jul. 6, 2004

(54) GINSENOSIDE CHEMOTHERAPY (75) Inventor: William Jia, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

(21) Appl. No.: 09/847,155

(22) Filed: May 1, 2001

(65) Prior Publication Data

US 2002/0013260 A1 Jan. 31, 2002

Related U.S. Application Data (60) Provisional application No. 60/204,785, filed on May 17, 2000.

(51) Int. Cl.$^7$ ............................................. A61K 31/56
(52) U.S. Cl. ...................................................... 514/171
(58) Field of Search ........................................ 514/171

(56) References Cited

U.S. PATENT DOCUMENTS

| | | |
|---|---|---|
| 4,157,894 A | 6/1979 | Bombardelli |
| 4,177,263 A | 12/1979 | Rosenberg et al. |
| 4,197,249 A | 4/1980 | Murdock et al. |
| 5,137,878 A | 8/1992 | Pang et al. |
| 5,200,534 A | 4/1993 | Rao |
| 5,202,448 A | 4/1993 | Carver et al. |
| 5,229,529 A | 7/1993 | Ueno et al. |
| 5,230,889 A | 7/1993 | Inoue |
| 5,274,137 A | 12/1993 | Nicolaou et al. |
| 5,279,949 A | 1/1994 | Nair |
| 5,283,253 A | 2/1994 | Holton et al. |
| 5,294,637 A | 3/1994 | Chen et al. |
| 5,589,182 A | 12/1996 | Tashiro et al. |
| 6,083,932 A | 7/2000 | Pang et al. |
| 6,156,291 A | 12/2000 | Pang et al. |

FOREIGN PATENT DOCUMENTS

| | | |
|---|---|---|
| EP | 590267 A2 | 6/1994 |
| JP | 08-291194 | 11/1996 |
| WO | WO 93/10076 | 5/1993 |
| WO | WO 93/23555 | 11/1993 |
| WO | WO 94/07876 | 4/1994 |
| WO | WO 94/07880 | 4/1994 |
| WO | WO 94/07881 | 4/1994 |
| WO | WO 94/07882 | 4/1994 |
| WO | WO 00/63219 | 10/2000 |

OTHER PUBLICATIONS

Nakata et al., Jpn. J. Cancer Res., (1998), 89(7), 733–740 Abstract Only.*

Tode et al., Mech. Cisplatin Resist. Its Circumvention (1998), 131–139 Abstract Only.*

Database WPI, Section Ch, Week 199703, Derwent Publications Ltd., London, GB; AN 1997–029530, XP002184631 & JP 08 291194 A, Abstract Only.

Han, Rui, Chinese Medical Sciences Journal, Recent Progress in the Study of Anticancer Drugs and Originating From Plants and Traditional Medicines in China 9:61–69, 1993.

Han, Rui, Stem Cells, Highlight on the Studies of Anticancer Drugs Derived from Plants in China 12:53–63, 1994.

Duda, Rosemary et al., Journal of Surgical Oncology, American Ginseng and Breast Cancer Therapeutic Agents Synergistically Inhibit MCF–7 Breast Cancer Cell Growth 72:230–239 1999.

Rosenberg et al., "Inhibition of Cell Division in Escherichia coli by Electrolysis Products from a Platinum Electrode," Nature, 205:698–699 (1965).

Rosenberg et al., "Template Deoxyribonucleic Acid and the Control of Replication," Nature, 206:999–1001 (1965).

Rosenberg et al, "Platinum Compounds: A New Class of Potent Antitumour Agents," Nature, 222:385–386 (1969).

Wani et al., "Plant Antitumor Agents. VI. The Isolation and Structure of Taxol, a Novel Antileukemic and Antitumor Agent from Taxus brevifolia$^{1,2}$," J. Am. Chem. Soc., Martin Styles, Ed., 93:9 pp. 2325–2327 (1971).

Schiff et al., "Promotion of Microtubule Assembly In Vitro by Taxol," Nature, 227:665–667 (1979).

Baum et al., "Taxol, Microtubule Stabilizing Agent, Blocks the Replication of Trypanosoma cruzi," Proc. Natl. Acad. Sci. USA, 78:7 pp. 4571–4575 (1981).

Kikuchi et al., "Inhibition of Human Ovarian Cancer Cell Proliferation In Vitro Ginsenoside $RH_2$ and Adjuvant Effects to Cisplatin In Vivo," Anti–Cancer Drugs, 2:63–67 (1991).

Stierle et al., "Taxol and Taxane Production by Taxomyces andreanae, an Endophytic Fungus of Pacific Yew," Science, 260:214–216 (1993).

Danesi et al., "Paclitaxel (Taxol) Inhibits Protein Isoprenylation and Induces Apoptosis in PC–3 Human Prostate Cancer Cells," Molecular Pharmacology, 47:1106–1111 (1995).

Dunn et al. "Mitoxantrone. A Review of its Pharamacological Properties and Use in Acute Nonlymphoblastic Leukaemia," Drugs and Aging, 9:2 pp. 122–147 (1996).

(List continued on next page.)

Primary Examiner—Rebecca Cook
(74) Attorney, Agent, or Firm—Townsend and Townsend and Crew LLP (57) ABSTRACT

The invention provides for the use of ginsenoside Rh2 in pharmaceutical compositions used in methods of inhibiting the multiplication of cancer cells, and methods of treating cancer in patients, comprising administering to such patients therapeutically and synergistically effective amounts of Rh2 in combination with a chemotherapeutic selected from the group consisting of paclitaxel and mitoxantrone. The cancer cells to be treated may be multidrug resistant. The cancer cells may for example be prostate cancer cells or breast cancer cells.

21 Claims, 5 Drawing Sheets

OTHER PUBLICATIONS

Haldar et al., "Taxol Induces bcl–2 Phosphorylation and Death of Prostate Cancer Cells[1]," *Cancer Research*, 56:1253–1255 (1996).

Nooter et al., "Molecular Mechanisms of Multidrug Resistance in Cancer Chemotherapy," *Path. Res. Pract.*, 192:768–780 (1996).

Ling, "Multidrug Resistance: Molecular Mechanisms and Clinical Relevance," *Cancer Chemother. Pharmacol.*, 40 (Suppl): S3–S8 (1997).

Wiseman and Spencer, "Mitoxantrone. A Review of its Pharmacology and Clinical Efficacy in the Management of Hormone–Resistant Advanced Prostate Cancer," *Drugs and Aging*, 10:6 pp. 473–485 (1997).

Liu, "Platinum(II) Complexes & Cisplatin," Copyright San Man Liu, www.ch.ic.ac.uk/local/projects/s_liu/Html/Cisplatin/html, (1998).

Blagosklonny et al., "Molecular Effects of Paclitaxel: Myths and Reality (A Critical Review)," *Int. J. Cancer*, 83:151–156 (1999).

van Brussel et al., "Chemosensitivity of Prostate Cancer Cell Lines and Expression of Multidrug Resistance–related Proteins," *European Journal of Cancer*, 35:4 pp. 664–671 (1999).

Wang et al., "The Effect of Antimicrotubule Agents on Signal Transduction Pathways of Apoptosis: A Review," *Cancer Chemother. Pharmacol.*, 44:355–361 (1999).

\* cited by examiner

GINSENOSIDE CHEMOTHERAPY

CROSS REFERENCES TO RELATED APPLICATIONS

This application claims priority to Canadian Patent Application No. 2,307, 393, filed May 1, 2001, and U.S. Provisional Patent Application No. 60/204,785, filed May 17, 2000, incorporated herein by reference in its entirety.

FIELD OF THE INVENTION

The invention is in the field of therapeutic compositions and methods, particularly chemotherapy of cancer using ginsenosides.

BACKGROUND OF THE INVENTION

Panax ginseng has served as an important component of traditional Chinese medicine for thousands of years. Recently, attention has been focused on the pharmacological activity of various compounds found in ginseng. As early as 1854, a saponin fraction was isolated from American ginseng, *Panax quinquefolium* L. In the late 1950s, saponin fractions collectively called ginsenosides were isolated from ginseng and structurally characterized. Ginsenosides are composed of a sugar portion (glycon) and a non-sugar portion (aglycon). Individual, isolated ginsenosides are commonly named according to the order of the Rf value of the compound on thin layer chromatograms (for example, Ra, Rb1, Rb2). By about the mid 1980s, a group of Rh ginsenosides were isolated. To date, at least four compounds, Rh1 to Rh4 have been isolated in the Rh group, each differentiated by the position of a glycon. Rh2 is a ginseng saponin with a dammarane skeleton that may be isolated from the root of *Panax ginseng* C. A. Meyer. Rh2 has the following formula, in which "Glc" is the glycon (glucose):

Rh2 may be available commercially, for example from Pegasus Pharmaceuticals Inc. (Vancouver, British Columbia, Canada). A wide variety of physiological effects have been attributed to ginsenosides, including Rh2, and the mechanism of action of these compounds and the range of potential therapeutic activities of each of the compounds remains uncertain.

Mitoxantrone is an antineoplastic agent which may be prepared as a synthetic antracenedione derivative of the anthraquinone dye ametantrone. Mitoxantrone has the following formula:

Mitoxantrone has reportedly been used in the treatment of a variety of malignant diseases, including acute non-lymphcytic leukaemia, advanced breast cancer and prostate cancer (see Wiseman and Spencer, *Drugs & Aging,* 1997 June 10(6): 473). Mitoxantrone is available commercially, and its preparation is for example described in U.S. Pat. No. 4,197,249; incorporated herein by reference.

Paclitaxel is a derivatized diterpenoid which may be obtained from the bark of the Pacific Yew and other natural sources (*Taxus brevifolia*, see Wani et al., *J. Am. Chem. Soc.* 93:2325, 1971; and Stierle et al., *Science* 60:214–216, 1993). Therapeutically, particularly in cancer therapy, paclitaxel is thought to act to stabilize microtubular structures by binding tubulin. As used herein, the word "paclitaxel" may include analogues, derivatives and conjugates of the naturally-occurring molecule, such as TAXOL™, TAXOTERE™, 10-desacetyl analogues of paclitaxel, 3'N-desbenzoyl-3'N-t-butoxy carbonyl analogues of paclitaxel, paclitaxel-PEG, paclitaxel-dextran, or paclitaxel-xylos. Paclitaxel may be prepared utilizing a variety of techniques (see WO 94/07882, WO 94/07881, WO 94/07880, WO 94/07876, WO 93/23555, WO 93/10076, U.S. Pat. Nos. 5,294,637, 5,283,253, 5,279,949, 5,274,137, 5,202,448, 5,200,534, 5,229,529, and EP 590267), or obtained from a variety of commercial sources, including for example, Sigma Chemical Co., St. Louis, Mo.

Cisplatin is an inorganic compound possessing a platinum element.

Cisplatin (cis-diaminedichloroplatinum (II)) has been used as a chemotherapeutic agent for many years since discovery of its antitumour activity (Rosenberg et al., *Nature,* 205:698, 1965; Rosenberg et al., Nature 222:385, 1969; U.S. Pat. No. 4,177,263). The mechanism of action of cisplatin in cancer therapy is believed to be through its ability to bind to DNA to interfere with repair mechanisms, causing cell death. Cisplatin has been reported to be effective in the treatment of a variety of cancers, most significantly in the treatment of ovarian and testicular cancer. Cisplatin is available commerically, for example, from Bristol-Myers Squibb Company under the commercial name PLATINOL™.

Cancerous tumors that have responded well initially to a particular drug or drugs, may later develop a tolerance to the drug(s) and cease responding, a phenomenon known as drug resistance. Multidrug resistance is generally characterized by cross-resistance of a disease such as cancer to more than one functionally or structurally unrelated drugs. Multidrug resistance may be caused by a number of mechanisms. For example, multidrug resistance may be mediated by a protein that is variously called multidrug-resistance 1 protein (MDR1), pleiotropic-glycoprotein (P-glycoprotein), Pgp or P170, referred to herein as "P-glycoprotein". P-glycoprotein is thought to be endogenous in cell membranes in certain drug resistant cells, multidrug resistant tumor cells, gastrointestinal tract cells, and the endothelial cells that form the blood brain barrier, where P-glycoprotein is thought to act as an efflux pump for the cell. Certain substances, including treatment drugs for various diseases, may be pumped out of the cell by the P-glycoprotein prior to having a therapeutic effect on the cell. There is accordingly a need for therapeutic approaches that may be used to counteract drug resistance, particularly multidrug resistance mediated by P-glycoprotein in cancer.

SUMMARY OF THE INVENTION

In one aspect, the invention provides methods inhibiting the multiplication of cancer cells, and methods of treating cancer in patients in need of such treatment, comprising administering to such patients therapeutically and synergistically effective amounts of Rh2 in combination with a chemotherapeutic selected from the group consisting of paclitaxel and mitoxantrone. The cancer cells to be treated may be multidrug resistant. The cancer cells may for example be prostate cancer cells or breast cancer cells.

In alternative aspects, the invention provides for the use of Rh2 in combination with a chemotherapeutic selected from the group consisting of paclitaxel and mitoxantrone to synergistically inhibit the multiplication of cancer cells, or to formulate a medicament for inhibiting the multiplication of cancer cells synergistically. The cancer cells to be treated may be multidrug resistant. The cancer cells may for example be prostate cancer cells or breast cancer cells.

In alternative aspects, the invention provides for the use of Rh2 to render non-P-glycoprotein multidrug resistant cancer cells (cancer cells that do not express P-glycoprotein) sensitive to a chemotherapeutic. In such embodiments, a chemotherapeutic may for example be used with Rh2 to treat a patient at a concentration or dosage at which the chemotherapeutic alone would otherwise not be effective in said non-P-glycoprotein multidrug resistant cancer cells. The chemotherapeutic may for example be paclitaxel, mitoxantrone, or cisplatin. The cancer cells may, for example, be prostate cancer cells or breast cancer cells.

In alternative aspects, the invention provides a pharmaceutical composition for the treatment of cancer, in patients in need of such treatment, comprising: a pharmaceutically acceptable carrier; and, therapeutically and synergistically effective amounts of Rh2 and a chemotherapeutic selected from the group consisting of paclitaxel and mitoxantrone.

DETAILED DESCRIPTION OF THE INVENTION

Cancers susceptible to treatment with Rh2 in combination with a chemotherapeutic in accordance with various aspects of the invention may include both primary and metastatic tumors and hyperplasias, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects of the invention, Rh2 in combination with a chemothrapeutic may also be useful in treating hematopoietic cancers such as leukemias (i.e., chloromas, plasmacytomas and the plaques and tumors of mycosis fungoides and cutaneous T-cell lymphoma/leukemia) and lymphomas (both Hodgkin's and non-Hodgkin's lymphomas). In addition, Rh2 in combination with a chemothrapeutic may be useful in the prophylactic prevention of metastases from the tumors described above.

Rh2 and the chemotherapeutic may be administered in combination separately or as one single combined pharmaceutical composition. The amount of each component administered may be determined by an attending clinician, taking into consideration a variety of factors such as the etiology and severity of the disease, the patient's condition and age and the potency of each component. The components may be administered in accordance with the standard methodologies as for example disclosed in the Physician's Desk Reference (PDR) published by Medical Economics Co. Inc. of Oradell, N.J.

A therapeutically and synergistically effective combination of Rh2 and a chemotherapeutic is characterized by the fact that the chemotheraputic is administered at a chemotherapeutic dosage and Rh2 is administered at a Rh2 dosage, and the therapeutic effect thereby achieved, such as inhibition of cellular multiplication, is greater than the sum of the therapeutic effect that would be achieved with the chemotherapeutic alone at the chemotherapeutic dosage plus the therapeutic effect that would be achieved with Rh2 alone at the Rh2 dosage. For example, a therapeutically and synergistically effective combination of Rh2 and paclitexal is a combination wherein the paclitexal is administered at a paclitexal dosage and Rh2 is administered at a Rh2 dosage, and the inhibition of cellular multiplication thereby achieved is greater than the sum of the inhibition that would be achieved with paclitexal alone at the paclitexal dosage plus the inhibition that would be achieved with Rh2 alone at the Rh2 dosage. Similarly, a therapeutically and synergistically effective combination of Rh2 and mitoxantrone is a combination wherein the mitoxantrone is administered at a mitoxantrone dosage and Rh2 is administered at a Rh2 dosage, and the inhibition of cancer cell multiplication thereby achieved is greater than the sum of the inhibition that would be achieved with mitoxantrone alone at the mitoxantrone dosage plus the inhibition that would be achieved with Rh2 alone at the Rh2 dosage.

One or more pharmaceutically acceptable carriers or exipients may be used to formulate pharmaceutical compositions of the invention, including solvents, dispersion media, coatings, antibacterial and antifungal agents, isotonic and absorption delaying agents, and the like that are physiologically compatible. In alternative embodiments, the carrier may be suitable for parenteral, intravenous, intraperitoneal, intramuscular, sublingual or oral administration. Pharmaceutically acceptable carriers may include sterile aqueous solutions or dispersions and sterile powders for the extemporaneous preparation of sterile injectable solutions or dispersion. Except insofar as any conventional media or agent is incompatible with the active compound, use thereof in the pharmaceutical compositions of the invention is contemplated. Supplementary active compounds can also be incorporated into the pharmaceutical compositions.

Pharmaceutical compositions typically must be sterile and stable under the conditions of manufacture and storage. The composition may be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the pharmaceutical compositions may be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating an active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Pharmaceutical compositions may be formulated with one or more compounds that enhance the solubility of the active compounds.

Procedures for the isolation and purification of ginsenoside Rh2 may for example include aqueous or organic extraction, column chromatography, thin-layer chromatography, and high performance chromatography. Techniques for the extraction and purification of plant extracts may be adapted for the preparation of Rh2 from the root of Panax ginseng C. A. Meyer, such as techniques disclosed in the following documents (which are incorporated herein by reference) U.S. Pat. No. 6,156,291 issued to Pang, et al. on Dec. 5, 2000; U.S. Pat. No. 6,083,932 issued to Pang, et al. on Jul. 4, 2000; U.S. Pat. No. 4,157,894 issued to Bombardelli on Jun. 12, 1979; U.S. Pat. No. 5,137,878 issued to Pang, et al. on Aug. 11, 1992; U.S. Pat. No. 5,230,889 issued to Inoue on Jul. 27, 1993; U.S. Pat. No. 5,589,182 issued to Tashiro, et al., on Dec. 31, 1996.

Although various embodiments of the invention are disclosed herein, many adaptations and modifications may be made within the scope of the invention in accordance with the common general knowledge of those skilled in this art. For example, the present invention comprehends all optical isomers and racemic forms of Rh2. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to".

EXAMPLE 1

Rh2 Synergistically Enhances the Cytotoxic Effect of Chemotherapy Agents

Figure 1:
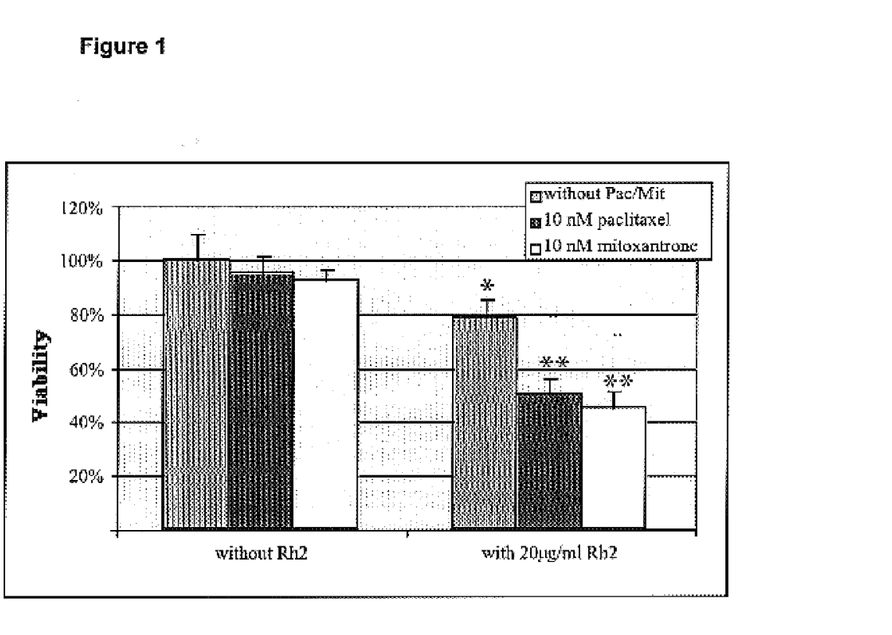
FIG. 1 includes two graphs, A and B, showing synergistic efficacy of Rh2 in combination with mitoxantrone (A) and with paclitaxel (B), showing cellular viability of human prostate cancer cells on the vertical axis and the chemotherapeutic concentration on the horizontal axis, with three lines on each graph, each line representing a different Rh2 concentration (0 µg/ml, 20 µg/ml and 30 µg/ml).
Figure 1A:
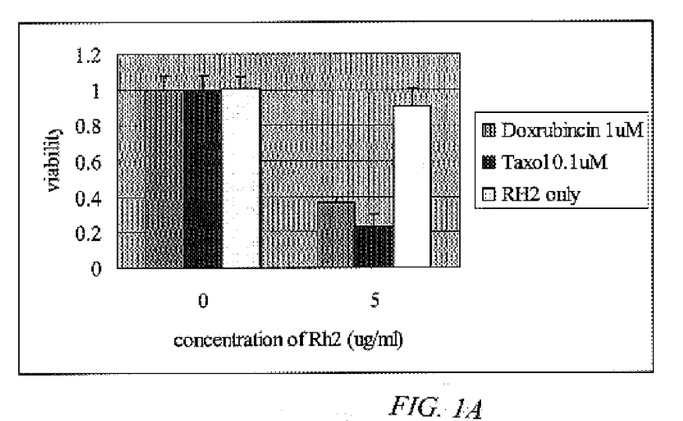
Figure 1B:
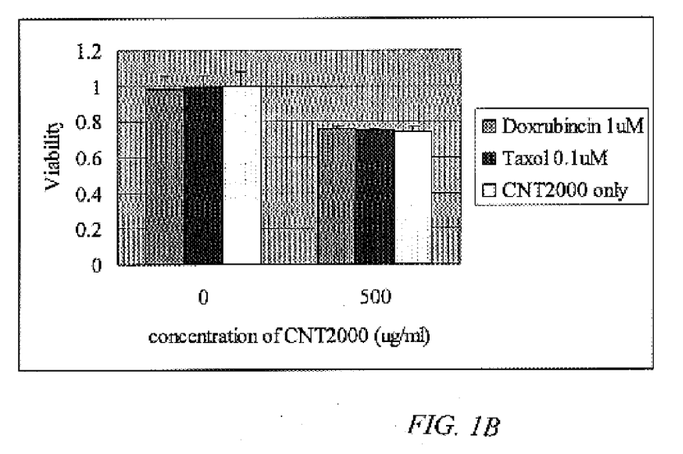

In one aspect, the invention provides therapeutically synergistic effects of Rh2 with chemotherapeutic compounds. In this example, human prostate cancer cells LNCaP were incubated with 0 $\mu$g/ml, 20 $\mu$g/ml and 30 $\mu$g/ml Rh2 in the presence of various concentrations of either mitoxantrone (FIG. 1A) or paclitaxel (FIG. 1B). At various concentrations of Rh2 and the chemotherapeutic compounds, an unexpected synergistic effect was seen with both mitoxantrone and paclitaxel. For example, 20 $\mu$g/ml of Rh2 showed little or no significant cytotoxicity alone, but added significantly to the cytotoxicity of mitoxatron over a wide range of mitoxantrone concentrations. Similarly, 20 $\mu$g/ml of Rh2 added significantly to the cytotoxicity of paclitaxel over a range of paclitaxel concentrations, particularly 0.1 nM and 1 nM paclitaxel.

EXAMPLE 2

Rh2 Sensitizes Drug-resistant Cells to Chemotherapy

Figure 2:
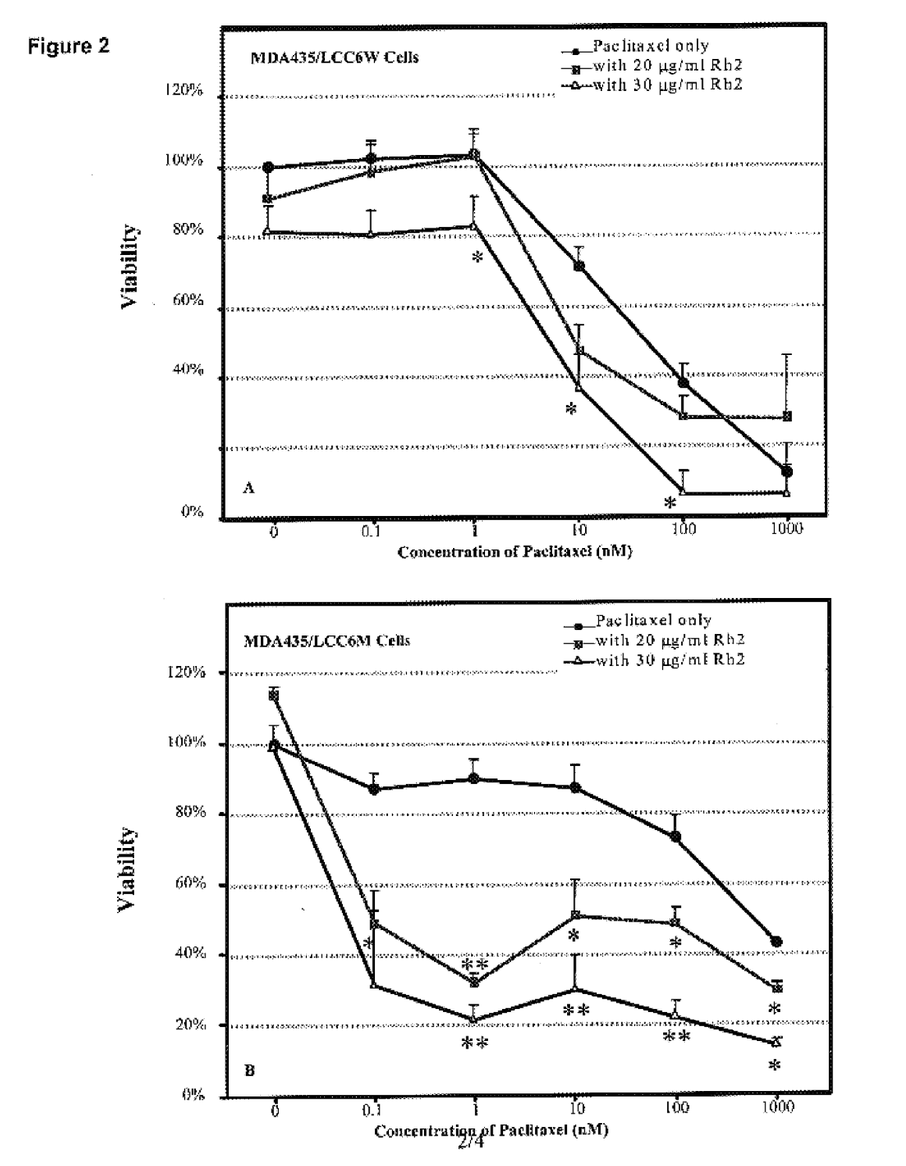
FIG. 2 includes two graphs, A and B, showing the use of Rh2 in combination with paclitaxel on wild-type breast cancer cells MDA435/LCC6W (A) and multidrug resistant breast cancer cells MDA435/LCC6M (B), showing cellular viability on the vertical axis and paclitaxel concentration on the horizontal axis, with three lines on each graph, each line representing a different Rh2 concentration (0 µg/ml, 20 µg/ml and 30 µg/ml) *p<0.001, **p<0.0002.

Human breast cancer cells MDA435/LCC6 cells, both wild-type (MDA435/LCC6W) or a drug resistant strain expressing a transfected multidrug resistant gene encoding P-glycoprotein (MDA435/LCC6M), were incubated with 20 $\mu$g/ml or 30 $\mu$g/ml of Rh2 in the presence of paclitaxel at various concentrations. Viable cells were counted 24 hrs after treatment. As shown in FIG. 2B, MDA435/LCC6M cells that express a multidrug resistance gene (MDR1), demonstrate a synergy between Rh2 and paclitaxel (FIG. 2B), wherein Rh2 alone had little or no effect on the cells, and the cytotoxicity of paclitaxel, particularly at lower concentrations of paclitaxel, is unexpectedly and significantly enhanced by Rh2. Cytotoxicity, in the multidrug resistant cells (MDA435/LCC6M), was for example shown in the presence of paclitaxel at a concentration as low as 0.1 nM, clearly showing that Rh2 sensitizes multidrug resistant cells to paclitaxel. Surprisingly, sensitization in some embodiments was greater in multidrug resistant cells, in that such cells were rendered susceptible to lower concentrations of chemotherapeutic than non multidrug resistant cells (MDA435/LCC6M). Table 1 showes calculated IC50s of paclitaxel with or without the Rh2 for the wild-type and multdrug resistant cell lines.

TABLE 1

Calculated IC50s of paclitaxel with or without Rh2 on MDA435/LCC6

|  | Paclitaxel alone | Pac. + 20 µg/ml Rh2 | Pac. + 30 µg/ml Rh2 |
|---|---|---|---|
| L6W | 248.00 nM | 75.00 nM | 25.00 nM |
| L6M | 631.00 nM | 0.15 nM | <0.03 nM |

In accordance with an aspect of the invention, Rh2 acts as a chemosensitizer in cancer cells with expressing multidrug resistance gene (MDR), rendering such cells susceptible to chemotherapeutic agents. As shown in this example, the chemosensitizing effect may be such that Rh2 and the chemotherapeutic compound, such as paclitaxel, may be used at concentrations which would not be therapeutically effective if either compound was applied alone.

EXAMPLE 3

Rh2 Sensitizes Non-Pgp Multidrug Resistant Cells to Chemotherapy

Figure 3:
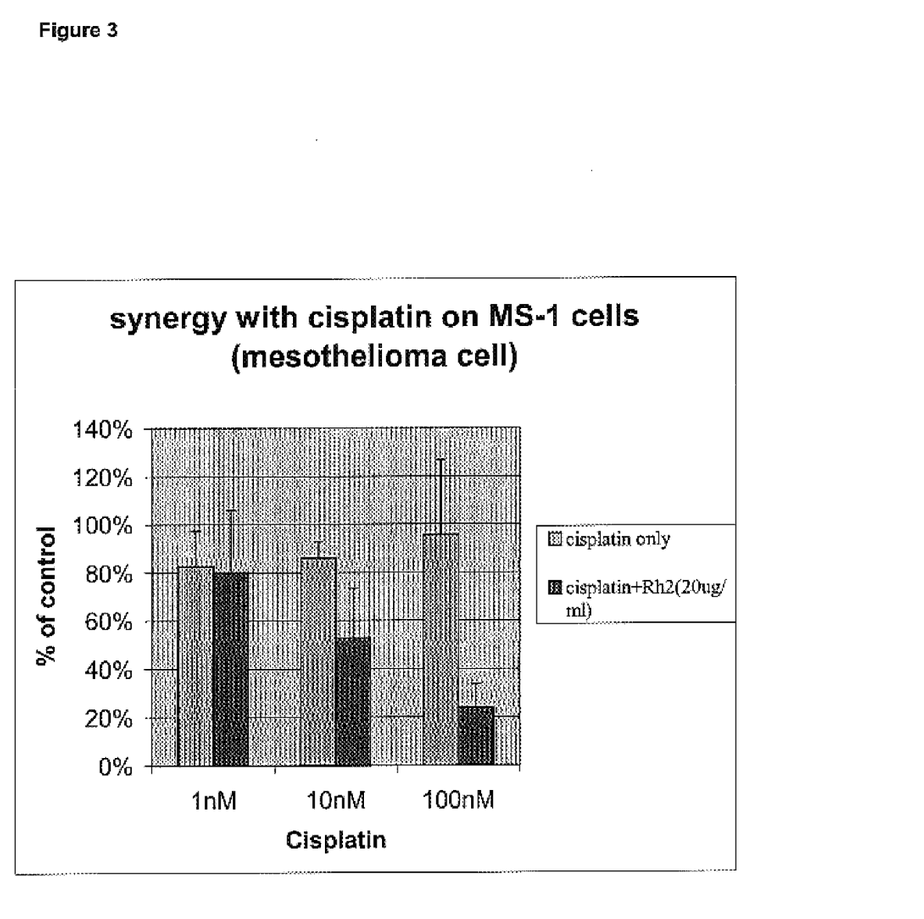
FIG. 3 is a graph showing the use of Rh2 in combination with cisplatin on multidrug resistant mesothelioma cells that do not express P-glycoprotein, showing (on the vertical axis) viability as a percent of control cell viability (controls are untreated mesothelioma cells) and showing cisplatin concentration on the horizontal axis.
Figure 4:
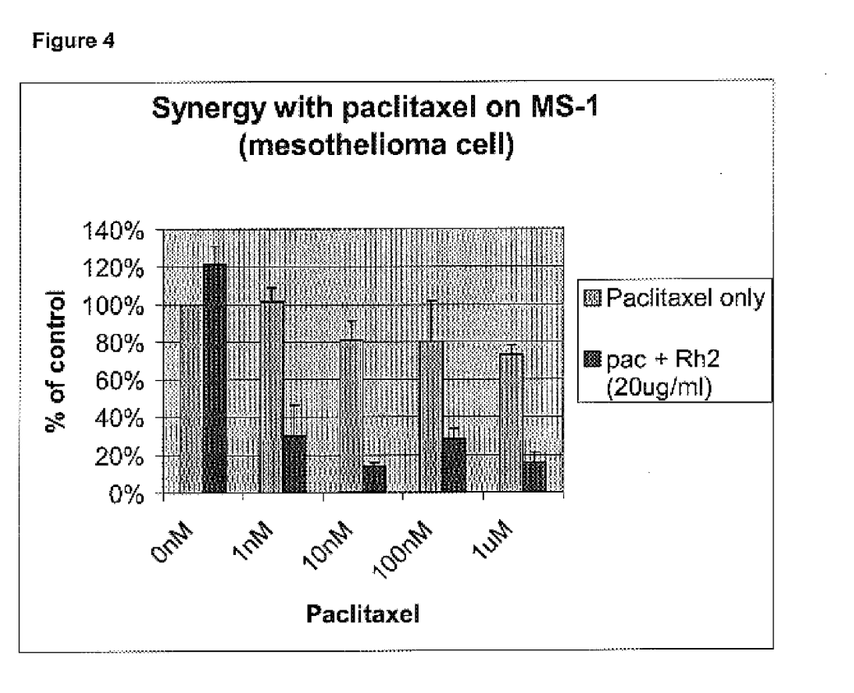
FIG. 4 is a graph showing the use of Rh2 in combination with paclitaxel on multidrug resistant mesothelioma cells that do not express P-glycoprotein, showing (on the vertical axis) viability as a percent of control cell viability (controls are untreated mesothelioma cells) and showing cisplatin concentration on the horizontal axis.

Mesothelioma cells that are highly resistant to paclitaxel and cisplatin but do not express P-glycoprotein (MS-1 cells), were incubated with 20 µg/ml of Rh2 in the presence of various concentrations of either cisplatin (FIG. 3) or paclitaxel (FIG. 4). As shown in FIGS. 3 and 4, the synergistic effect of Rh2 with both cisplatin and paclitaxel was significant in the non-Pgp multidrug resistant cells.

What is claimed is:

1. A method of inhibiting the multiplication of cancer cells selected from the group consisting of prostate cancer cells and breast cancer cells comprising treating the cells with a therapeutically and synergistically effective combination of paclitaxel and isolated ginsenoside Rh2.

2. The method of claim 1, wherein the cancer cells are multidrug resistant.

3. The method of claim 1, wherein the cancer cells do not express P-glycoprotein.

4. The method of claim 1, wherein the cancer cells are breast cancer cells.

5. The method of claim 2, wherein the cancer cells are breast cancer cells.

6. The method of claim 1, wherein the cancer cells are prostate cancer cells.

7. The method of claim 2 wherein cells are prostate cancer cells.

8. A method of treating a cancer selected from the group consisting of breast cancer and prostate cancer, in a patient in need therapy comprising treating the patient with a therapeutically and synergistically effective combination of paclitaxel and isolated ginsenoside Rh2.

9. The method of claim 8, wherein the cancer is a multidrug resistant cancer.

10. The method of claim 9, wherein the cancer is prostate cancer.

11. The method of claim 9, wherein the cancer is breast cancer.

12. The method of claim 8, wherein the cancer is breast cancer.

13. The method of claim 8, wherein the cancer is prostate cancer.

14. A method of inhibiting the multiplication of multidrug resistant cancer cells, selected from the group consisting of prostate cancer cells and breast cancer cells wherein the cells do not express P-glycoprotein, and wherein paclitaxel alone is not therapeutically effective to inhibit the multiplication of the cells, comprising treating the cells with a therapeutically and synergistically effective combination of isolated ginsenoside Rh2 and paclitaxel.

15. The method of claim 14, wherein the multidrug resistant cancer cells are breast cancer cells.

16. The method of claim 14, wherein the multidrug resistant cancer cells are prostate cancer cells.

17. A pharmaceutical composition comprising a pharmaceutically acceptable carrier and therapeutically and synergistically effective amounts of isolated ginsenoside Rh2 and paclitaxel.

18. The pharmaceutical composition of claim 17, wherein the form of the composition is selected from the group consisting of an orally administrable form, an injectable form, and an externally applicable form.

19. The pharmaceutical composition of claim 18, wherein the composition is the orally administrable form and is selected from the group consisting of a tablet, a powder, a suspension, an emulsion, a capsule, a granule, a troche, a pill, a liquid, a spirit, a syrup and a limonade.

20. The pharmaceutical composition of claim 18, wherein the composition is the injectable form and is selected from the group consisting of a liquid, a suspension and a solution.

21. The pharmaceutical composition of claim 18, wherein the composition is the externally applicable form and is selected from the group consisting of an ointment, a liquid, a powder, a plaster, a suppository, an aerosol, a liniment, a lotion, an enema and an emulsion.

* * * * *